(12) United States Patent
Banerjee et al.

(10) Patent No.: US 7,384,789 B2
(45) Date of Patent: Jun. 10, 2008

(54) DIVALENT METAL ION SENSORS AND BINDERS

(75) Inventors: Anamitro Banerjee, Grand Forks, ND (US); Julius N. Ngwendson, Grand Forks, ND (US)

(73) Assignee: The University of North Dakota, Grand Forks, ND (US)

( * ) Notice: Subject to any disclaimer, the term of this patent is extended or adjusted under 35 U.S.C. 154(b) by 0 days.

(21) Appl. No.: 11/699,615

(22) Filed: Jan. 30, 2007

(65) Prior Publication Data

US 2007/0179311 A1    Aug. 2, 2007

Related U.S. Application Data

(60) Provisional application No. 60/766,587, filed on Jan. 30, 2006.

(51) Int. Cl.
*G01N 33/20* (2006.01)
*C07C 229/00* (2006.01)
(52) U.S. Cl. .......................... 436/81; 436/73; 562/433
(58) Field of Classification Search ............... None
See application file for complete search history.

(56) References Cited

U.S. PATENT DOCUMENTS

| 5,308,754 | A | * | 5/1994 | Kankare et al. ............. 435/7.4 |
| 5,376,552 | A | * | 12/1994 | Tokuda et al. ................ 436/73 |
| 5,501,980 | A | | 3/1996 | Katerinopoulos et al. |
| 6,030,840 | A | | 2/2000 | Mullinax et al. |
| 6,586,256 | B1 | | 7/2003 | Glass et al. |
| 2002/0055091 | A1 | | 5/2002 | Thompson et al. |
| 2003/0008405 | A1 | | 1/2003 | Lippard et al. |
| 2003/0109056 | A1 | | 6/2003 | Vossmeyer et al. |

OTHER PUBLICATIONS

Anales de Quimica (1968-1979) (1968), 64(1), 47-54.*
Trace and Residue Analysis in Kirkl Othmer Encyclopedia of Chemical Technology, Copyright© 1997 by John Wiley & Sons, pp. 1-27, article online posting date: Dec. 4, 2000.*

* cited by examiner

*Primary Examiner*—Karl Puttlitz
(74) *Attorney, Agent, or Firm*—Kinney & Lange, P.A.

(57) ABSTRACT

Diamino polyacetate benzene compounds are used as a selective fluorescence probe, sensor, or binders for divalent metal ions. The compounds provide for uses as divalent metal ion sensors in diagnostic applications and binders for environmental and medical treatments.

11 Claims, 4 Drawing Sheets

DIVALENT METAL ION SENSORS AND BINDERS

CROSS-REFERENCE TO RELATED APPLICATION(S)

This application claims benefit under 35 U.S.C. § 119(e) of U.S. Provisional Application No. 60/766,587, filed Jan. 30, 2006, entitled ZINC SENSORS AND BINDERS, which is incorporated by reference.

BACKGROUND

With increased awareness for the detrimental impact of metals on human health and environment, it is highly desirable to develop more sensitive and selective probes for the detection of metal ions in biological and environmental samples. A variety of divalent metal ions are known to be involved in the structural, catalytic, and regulatory aspects of the biological system, and some such metal ions serve as prognostics of certain human diseases. For example, $Cu^{2+}$, $Zn^{2+}$, and $Fe^{2+}$ have been found to be involved in aggregating β-amyloid peptides during the onset of the Alzheimer's disease. However, due to the lack of metal ion specific probes, the relative contribution of one type of metal ion versus the other in causing the disease is not clearly understood. The inability to differentiate among different types of divalent metal ions in biological samples has been one of the major impediments in the area of bio-analytical chemistry.

Although there has been some success in detection of biologically significant metal ions by developing fluorescence probes (e.g., fura-2 for $Ca^{2+}$), most of the probes exhibit cross reactivity for other metal ions. This is not surprising since both physical and electronic properties of these metal ions are not too disparate, and they tend to exhibit comparable binding affinities with their cognate chelating agents. Consequently, not only synthetic (organic) probes but also enzymatic probes exhibit cross-reactivities among metal ions. Presently, quinoline-sulfonamide containing compounds and their derivatives are regarded to be as the "gold" standards for detecting low concentrations of $Zn^{2+}$, albeit such compounds also exhibit selectivity for $Cu^{2+}$. The origin of such selectivity appears to be encoded by facile changes in the coordination state of $Zn^{2+}$ versus $Cu^{2+}$. Unexpectedly, the invention herein describes a method for the synthesis and use of novel $Zn^{2+}$ selective fluorescent compounds that exhibit a high specificity for $Zn^{2+}$ with low reactivity to other divalent metal ions.

BRIEF SUMMARY

The present invention described herein is a method used for the detection of metal ions in biological or environmental samples using new compounds that fluoresce upon binding to the metal ions. The synthetic backbone of these compounds is a diamino polyacetate benzene that is modified using various alkyl moieties to provide metal ion specificity. The diamino polyacetate benzene compounds synthesized exhibit preferential binding to a select metal ion and their fluorescent properties upon binding provide for a new class of organic compounds that act as selective sensors for diagnostic and detection applications. One such diamino polyacetate benzene showed high specificity as a $Zn^{2+}$ selective fluorescence probe or sensor relative to other metal ions. The diamino polyacetate benzene compounds provide for uses as zinc selective binders that have utility for environmental clean-up and control of zinc in health and medical treatments.

DETAILED DESCRIPTION

Figure 1:
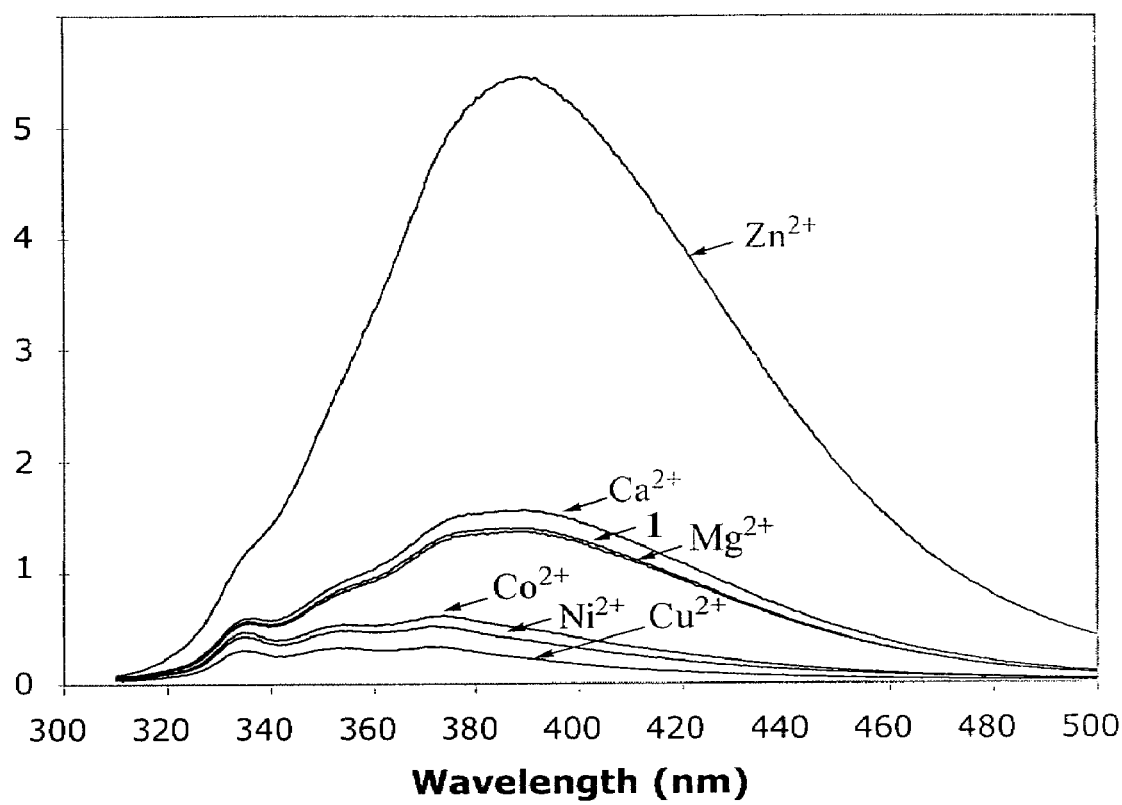
FIG. 1: Fluorescence emission spectra of compound 1.

In the present invention novel diamino polyacetate benzene compounds were synthesized that demonstrated high selective properties for a divalent metal ion relative to other divalent metal ions. These diamino polyacetate benzene compounds exhibited highly desirable properties that were advantageous as a zinc sensor for metal ion detection in biological and environmental samples containing other divalent metal ions. Other properties exhibited of the complexed diamino polyacetate benzene compounds that were insoluble as compared to the readily soluble uncomplexed compound provided for utility in the removal of zinc from environmental and waste materials as well as potential use as a therapeutic agent for the treatment of zinc based diseases.

Cai et al. synthesized a N,N,N',N'-tetrakis(carboxylatemethyl)-2,6-diaminocresol compound that had properties as a divalent metal binding probe. Cai, L.; Xie, W.; Mahmoud, H.; Han, Y.; Wink, D. J.; Li, S.; O'Connor, C. J. Inorg. Chim, Acta 1997, 263, 231-245. The structure that it formed contained a five coordinate trigonal bipyramidal that showed binding to only $Co^{2+}$ or $Cu^{2+}$. The ligand-metal conjugate yielded a charge-transfer band around 300 nm. The structural data showed that the primary binding involved carboxyl and amino groups.

In our analysis, the diamino polyacetate benzene appeared to be involved in the coordination bond with either $Co^{2+}$ or $Cu^{2+}$ while the latter metal exhibited a distorted configuration. To improve spectral properties and blinding characteristics for divalent metal ions of the diamino polyacetate benzene as a modifier of coordinate geometry, compounds were synthesized {[3-(biscarboxymethylamino)-2-methoxy-5-methylphenyl]carboxymethylamino}acetic acid (compound 1) in which the phenolic oxygen was modified. As described herein, these novel compounds provide for improved properties and utility as selective sensors and binding agents in a variety of applications.

EXAMPLE 1

Synthesis of Novel Diamino Polyacetate Alkoxy Benzene Compounds: Potassium-2,6-diamino-(N,N, N',N'-tetraacetate)-4-methylanisole (Compound 1)

Commercially available reagents, obtained from Acros Organics and Aldrich were used as received. All solvents were distilled before use. Reactions were monitored by thin-layer chromatography (TLC) and visualization was accomplished with a UV lamp. Reaction mixtures were purified by column chromatography, performed with the indicated solvents using silica gel (230-400 mesh). The $R_f$ values were calculated based on the eluents used for purification. The yields reported refer to chromatographically and spectroscopically pure compounds. The purity of the compounds were ascertained by GC/MS analysis (HP 5890 Series II GC fitted with HP 5971 Series Mass Selective Detector). $^1$H and proton decoupled $^{13}$C NMR spectra were recorded on a Bruker AMX 500 MHz spectrometer at ambient temperature. The fluorescence spectra were obtained using Jobin Yvon Horiba Fluorolog-3 spectrofluorometer. The HEPES buffer was prepared from commercially available 1M solution of the free acid and the pH was adjusted to 7.0 by the addition of KOH pellets in the presence of 0.135 M NaCl. The fluorescence measurements were carried out on 3 mL samples of the sensor and 3 μL aliquots of the 200 mM metal ion solution in HEPES were added to the sample to make up the desired metal concentrations.

2,6-Diamino-4-methylanisole hydrochloride. 2-Methoxy-5-methyl-1,3-dinitrobenzene (0.050 g, 0.236 mmol) was suspended in conc. Hydrochloric acid (1.2 mL). Tin granules (0.118 g, 0.995 mmol) were added slowly to the mixture with stirring at room temperature. After 2 hours, the solution turned white (all the tin granules were dissolved), the solution was cooled to 4° C. The product was collected as a white precipitate and recrystallized from hot water-concentrated hydrochloric acid. Yield=0.037 g (70%) from 0.050 g 2-Methoxy-5-methyl-1,3-dinitrobenzene. White flakes; mp 226° C. (dec); $^1$H NMR (DMSO) δ: 6.57 (s, 2H), 3.91 (s, broad, 6H), 3.72 (s, 3H), 2.17 (s, 3H).

2,6-Diamino-4-methyl anisole. 2,6-Diamino-4-methylanisole hydrochloride (0.100 g, 0.443 mmol) was suspended in 3 mL of $CH_2Cl_2$ under $N_2$. The solution was cooled in ice-water bath to 0° C. Concentrated ammonium hydroxide solution (0.4 mL) was slowly added using a syringe. The mixture was stirred for 10 mins as $NH_4Cl$ precipitated out, and washed with water. The organic layer was dried with anhydrous sodium sulfate and the solvent was removed under reduced pressure. GC-MS analysis indicated a pure product. Yield=0.067 g (100%) from 0.100 g 2,6-Diamino-4-methylanisole hydrochloride; viscous oil; $^1$H NMR ($CDCl_3$) δ: 6.02 (s, 2H), 3.76 (s, 3H), 3.67 (s, broad, 4H), 2.16 (s, 3H). $^{13}$C NMR ($CDCl_3$) δ: 139.8, 134.8, 132.9, 107.3, 58.7, 21.3; EI-MS, m/z (rel. intensity) 153 (M+1, 5.0), 152 (M+, 49.8), 138 (7.6), 137 (100), 124 (1.7), 110 (8.8), 109 (16.4), 92 (4.3), 80 (3.2), 79 (1.2), 65 (2.7), 54 (0.5).

Ethyl-2,6-diamino-(N,N,N',N'-tetraacetate)-4-methylanisole (1'). 2,6-Diamino-4-methylanisole (0.100 g, 0.799 mmol), KI (0.436 g, 2.63 mmol), $K_2HPO_4$ (0.458 g, 2.63 mmol), and ethyl bromoacetate (0.33 mL, 2.9 mmol) were mixed in a 250-mL flask with 10 mL of acetonitrile. The mixture was refluxed for 15 h under $N_2$ then freshly dried molecular sieves and more base were added. The mixture was refluxed for another 18 h. The mixture was cooled and the solvent was removed under reduced pressure. The residue was dissolved in hexane-ethyl acetate mixture (7:3) and filtered through silica gel. The filtrate was distilled in vacuo, and the residue was purified on a column of silica gel using hexane-ethyl acetate (9:1). The fractions were distilled and the oily product was crystallized from hexane-ethyl acetate (95:5) mixture to give pure products (analyzed by GC-MS). Yield=0.170 g (52%) from 0.100 g of 2,6-Diamino-4-methylanisole. White needles; mp 67-69° C.; $^1$H NMR ($CDCl_3$) δ: 6.27 (s, 2H), 4.18 (q, J=7.2 Hz, 8H), 4.13 (s, 8H), 3.68 (s, 3H), 2.19 (s, 3H), 1.27 (t, J=7.2 Hz, 12H). $^{13}$C NMR ($CDCl_3$) δ: 171.6, 143.7, 141.3, 133.4, 113.5, 60.8, 59.7, 54.0, 21.9, 14.5; EI-MS, m/z (rel. intensity) 498 (M+2, 0.6), 497 (M+2, 2.6), 496 (M+, 11.2), 465 (2.0), 424 (19.3), 423 (75.4), 335 (16.6), 321 (4.4), 307 (2.1), 2 93 (2.4), 277 (4.0), 264 (18.1), 263 (100), 249 (3.6), 247 (3.8), 235 (10.1), 219 (4.4), 191 (16.1), 175 (36.8), 162 (15.4), 161 (15.4), 148 (11.2), 134 (5.8), 118 (5.3), 91 (3.5), 59 (9.8).

Potassium-2,6-diamino-(N,N,N',N'-tetraacetate)-4-methylanisole (1). Compound 1' (0.038 g, 0.077 mmol) was dissolved in 2 mL of MeOH under stirring. Aqueous KOH (0.1 mL, 3M) was added to the mixture and refluxed for 4 h. The reaction mixture was then cooled and the solvent removed to obtain a brown hygroscopic solid. Yield=0.040 g (96%) from 0.038 g of compound 1. $^1$H NMR ($D_2O$) δ: 6.13 (s, 2H), 3.85 (s, 8H), 3.57 (s, 3H), 2.16 (s, 3H). $^{13}$C NMR ($D_2O$) δ: 180.5, 145.1, 138.3, 133.6, 109.7, 59.7, 57.1, 21.1.

Zinc-2,6-diamino-(N,N,N',N'-tetraacetate)-4-methylanisole. The sodium salt equivalent of 1 (30 mg, 0.06 mmol) was dissolved in 0.75 mL $D_2O$ and the $^1$H NMR was taken. Then $ZnCl_2$ (8 mg, 0.06 mmol) was added and the solution was stirred. Some of the complex precipitated out and it was filtered before the $^1$H NMR was taken again. $^1$H NMR ($D_2O$) δ: 6.18 (s, 2H), 3.89 (s, 8H), 3.63 (s, 3H), 2.22 (s, 3H).

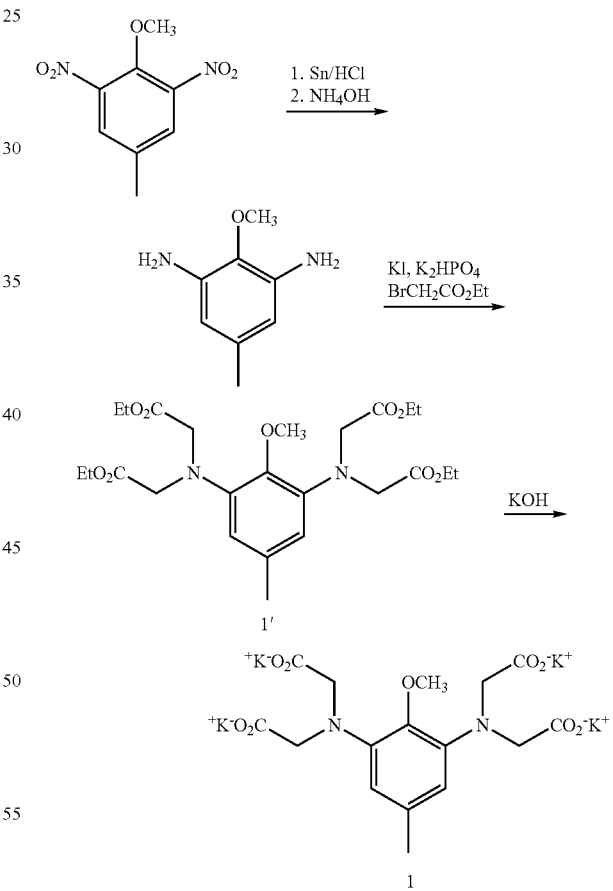

Derivatives of compound 1 involve the phenolic oxygen by substituting the methyl group with groups that are alkylated, which but are not limited to, ethyl, isopropyl, t-butyl, benzyl, substituted benzyl, and phenethyl, and electron withdrawing groups which include, but are not limited to, trifluoromethyl and acyl($COCH_3$). The acyl derivatives provide additional oxygen that interact with the metal ion.

EXAMPLE 2

Fluorescence Profile of Potassium-2,6-diamino-(N,N,N',N'-tetraacetate)-4-methylanisole (Compound 1)

The influence of divalent metal ions on the fluorescence spectral profile of compound 1 is shown in FIG. 1, where the fluorescence emission spectra of 200 µM compound 1 ($\lambda_{ex}$=300 nm) with stoichiometric concentrations of selected divalent metal ions. Compound 1 has a weak fluorescence emission peak around 386-390 nm, which is differently affected by different metal ions. The emission intensity of compound 1 (at 390 nm) was barely affected in the presence of $Mg^{2+}$ and only slightly increased in the presence of $Ca^{2+}$. In contrast, the fluorescence intensity of compound 1 decreases in the presence of $Cu^{2+}$, $Ni^{2+}$, and $Co^{2+}$. The most dramatic effect of fluorescence profile of compound 1 was observed in the presence of $Zn^{2+}$.

Surprisingly, in the presence of stoichiometric concentration of $Zn^{2+}$ the fluorescence emission intensity of compound 1 was increased by about 10 fold. Such an enhancement in fluorescence intensity is not kinetically controlled as the time dependent incubation of $Zn^{2+}$ with compound 1 and its emission intensity was not altered. This deduction was equally valid for the interaction of other metal ions with compound 1, irrespective of their spectral modulating features.

Unexpectedly, the $Zn^{2+}$-induced fluorescence enhancement of compound 1 was maintained even in the presence of a 100 fold excess of $Ca^{2+}$. The unique properties of compound 1 can be utilized to detect $Zn^{2+}$ in the physiological milieu containing the high concentrations of $Ca^{2+}$. These results demonstrated that compound 1 was a $Zn^{2+}$ specific fluorescent probe that has application as a novel divalent zinc sensor.

EXAMPLE 3

Binding Kinetics of Potassium-2,6-diamino-(N,N,N',N'-tetraacetate)-4-methylanisole (Compound 1)

Figure 2:
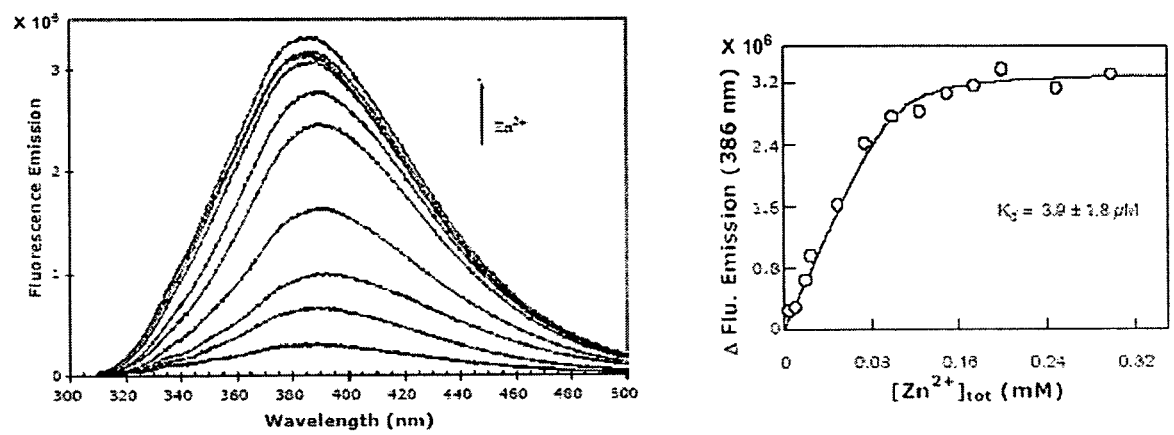
FIG. 2: Fluorescence emission spectra of 100 μM of compound 1 in the presence of different concentrations of $Zn^{2+}$. $K_d$ value of 3.9±1.8 μM.

To determine the magnitude of $Zn^{2+}$ induced fluorescence spectral changes of compound 1 as well as its binding affinity, a detailed spectrofluorometric titration study was performed. In FIG. 2 (right panel) shows the fluorescence emission spectra of compound 1 (corrected for the buffer) as a function of increasing concentrations of $ZnCl_2$. The fluorescence emission intensity at 386 nm ($\lambda_{ex}$=300 nm) showed a saturating profile as a function of $ZnCl_2$ (FIG. 2, left panel). Since the concentration of compound 1 was comparable to the initial concentrations of $Zn^{2+}$, the binding constant of compound 1-$Zn^{2+}$ complex was calculated by a complete solution of the quadratic equation, describing their interaction. The solid line was the best fit of the experimental data for the $K_d$ value of 6.1±2.5 µM and the stoichiometry of 1:1 (i.e. 1 mole of bound $Zn^{2+}$ per mol of compound 1).

The basis of compound 1 (vis a vis analogous compounds reported in the literature) functioning as $Zn^{2+}$ selective fluorescent sensor was unexpected. It has been well established that unlike $Cu^{2+}$, $Co^{2+}$, and $Ni^{2+}$, which predominate either as the square planer or tetrahedral coordination state, $Zn^{2+}$ preferentially exists in the octahedral state. Because of its octahedral state, zinc can interact with all six groups that are contributed by the two iminodiacetate moieties of compound 1. The stoichiometry of compound 1-$Zn^{2+}$ complex is equal to 1:1 (FIG. 2).

EXAMPLE 4

Solubility of Potassium-2,6-diamino-(N,N,N',N'-tetraacetate)-4-methylanisole (Compound 1)

In contrast to readily soluble compound 1, the compound 1-Zn complex has low solubility in water and methanol. All attempts at recrystallization of the complex resulted in the formation of a white powder. Saturated solution of the complex in $D_2O$ was subjected to 1H NMR analysis in an attempt to elucidate the structure of the complex. Comparison of the $^1$H NMR of the compound 1 and its 1:1 mixture with Zn(II) indicated that the zinc binding induces a deshielding effect on all the protons, accompanied by substantial peak broadening. The broadening of the peaks imply that the complex was fluxional, which explained the poor recrystallization properties.

Compound 1 was found to have a high solubility in the aqueous medium, which made it an ideal compound as a selective fluorescence probe (sensor) for detection of $Zn^{2+}$ in biological samples. Moreover, its high solubility made the compound an attractive therapeutic for the treatment of medical diseases where an excess of Zn or Zn containing proteins is a causative agent of the disease. In contrast, the low solubility of the complex would be useful in extracting $Zn^{2+}$ ions from environmental matrix, when high concentrations of Zn are present.

EXAMPLE 5

Synthesis of Novel Diamino Polyacetate Benzene Compounds: Sodium-1,3-diamino-(N,N,N',N'-tetraacetate)benzene (Compound 3)

In order to determine the structural requirements for these sensors to detect $Zn^{2+}$, compound 3 was synthesized such that only two IDA groups were present (structurally similar to compound 1 except that the methoxy group was absent).

Ethyl-1,3-diamino-(N,N,N',N'-tetraacetate)benzene (3'). 0.211 g (2.00 mmol) of 1,3-phenylenediamine, 1.661 g (10.0 mmol) of KI, 1.742 g (10.0 mmol) of $K_2HPO_4$, 1.13 mL (10.0 mmol) of ethyl bromoacetate, 15 mL of MeCN and freshly dried molecular sieves were used. The reaction was refluxed for 27 h. The mixture was cooled and the solvent was removed under reduced pressure. The residue was dissolved in hexane/ethyl acetate (7:3) and filtered through silica gel. The filtrate was distilled in vacuo and purified on column chromatography using hexane/ethyl acetate (95:1) mixture. Yield=0.488 g (56%). Colorless oil; $^1$H NMR ($CDCl_3$) δ: 7.06 (t, J=7.9 Hz, 1H, Ar—H), 6.08 (d, J=7.9 Hz, 2H, Ar—H), 5.85 (s, 1H, Ar—H), 4.21 (q, J=7.3 Hz, 8H, C—$CH_2$—C), 4.10 (s, 8H, N—$CH_2$—C), 1.27 (t, J=7.3 Hz, 12H, —$CH_3$). $^{13}$C NMR ($CDCl_3$) δ: 171.2, 149.3, 130.2, 103.6, 97.7, 61.3, 53.9, 14.4.

Sodium 1,3-diamino-(N,N,N',N'-tetraacetate)benzene (3). Compound 3' (0.047 g, 0.104 mmols) was dissolved in 30 mL of MeOH/$H_2O$ (2:1). 0.139 g (3.48 mmols) of NaOH was added. The solution was stirred at room temperature overnight. Evaporation of the solvent mixture was followed by suspension of the residue on methanol. The solution was filtered and methanol was evaporated under reduced pressure. The residue was dissolved in minimum water and dried under vacuum to remove trapped methanol. Brown powder. Yield=0.038 g (84%). $^1$H NMR ($D_2O$) δ: 7.04 (t, J=8.2 Hz, 1H, Ar—H), 5.88 (d, J=8.2 Hz, 2H, Ar—H), 5.59 (s, 1H, Ar—H), 3.84 (s, 8H, —$CH_2$—). 6.98-6.96 (m, 1H, Ar—H), 6.89-6.87 (m, 2H, Ar—H), 6.74-6.72 (m, 1H, Ar—H), 3.78 (s, 4H, —CH$_2$—), 3.77 (s, 3H, O—CH$_3$). $^{13}$C NMR (D$_2$O) δ: 180.2, 150.1, 130.3, 101.0, 95.0, 55.8.

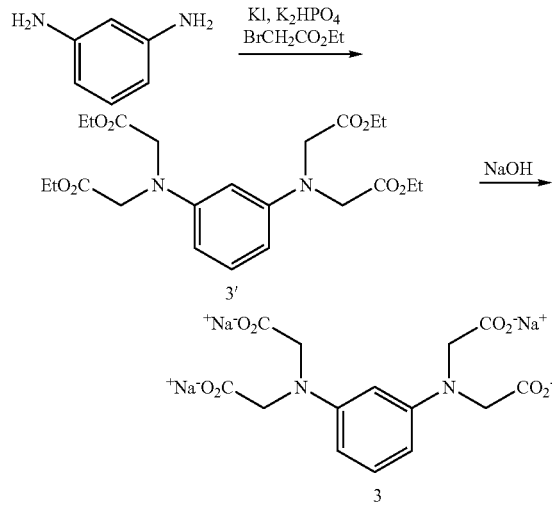

EXAMPLE 6

Fluorescence Profile of Sodium 1,3-diamino-(N,N,N',N'-tetraacetate)benzene (Compound 3)

Figure 3:
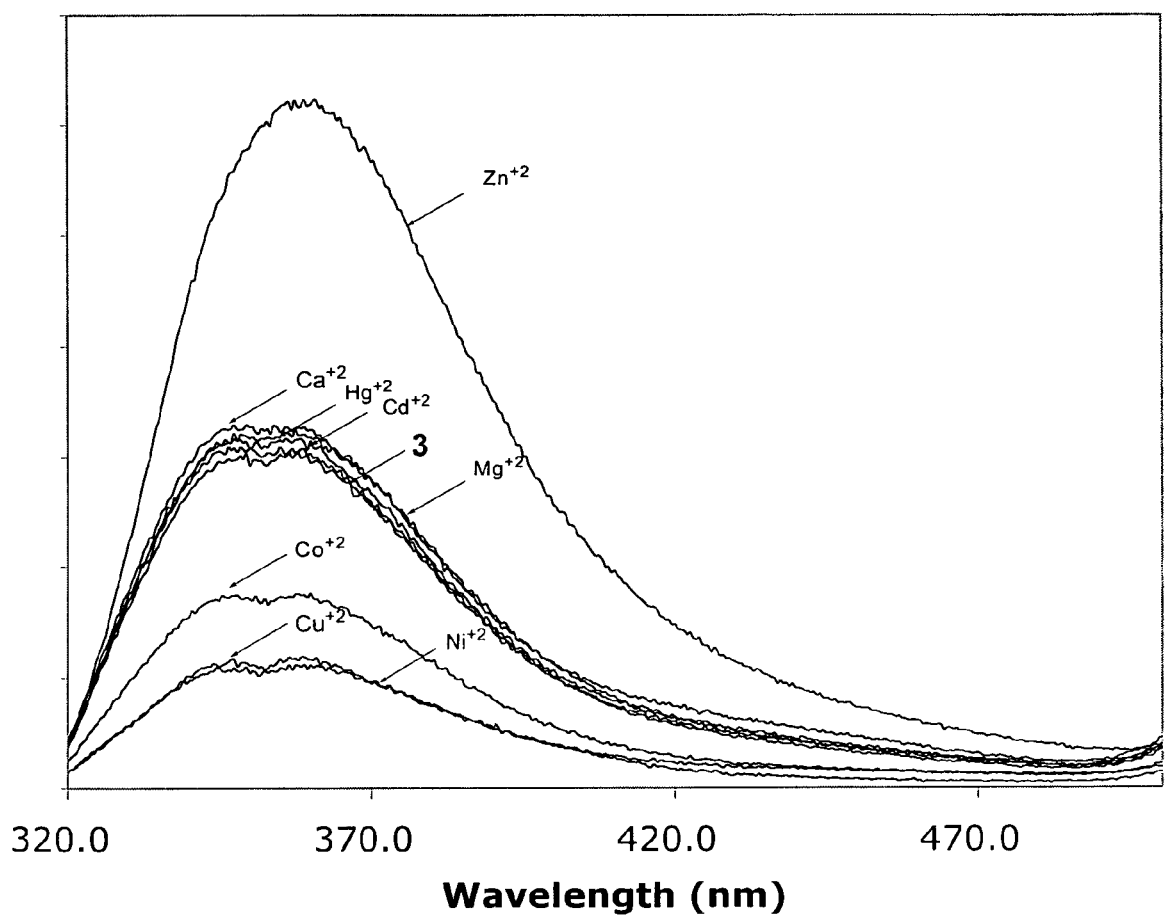
FIG. 3: Fluorescence emission spectra of compound 3.

The influence of divalent metal ions on the fluorescence spectral profile of compound 3 is shown in FIG. 3, where the fluorescence emission spectra of 200 µM compound 1 (λ$_{ex}$=315 nm) with stoichiometric concentrations of selected divalent metal ions. Compound 3 has a weak fluorescence emission peak around 355-360 nm, which is differently affected by different metal ions. The emission intensity of compound 3 (at 357 nm) was slightly enhanced in the presence of Mg$^{2+}$, Ca$^{2+}$, Cd$^{2+}$, and Hg$^{2+}$. In contrast, as expected, the fluorescence intensity of compound 3 decreases in the presence of Cu$^{2+}$, Ni$^{2+}$, and Co$^{2+}$. However, in the presence of Zn$^{2+}$, the fluorescence of the compound is enhanced significantly (similar to compound 1). Titration of compound 3 with Zn$^{2+}$ indicates a K$_d$ value of 2 mM (approx.). These results indicate that the four acyl groups are crucial for the sensor to detect Zn$^{2+}$, while the methoxy group helps in red shift of the fluorescence emission wavelength and a higher binding constant.

EXAMPLE 7

Derivatives that can Fluoresce Visible Light: Sodium 2,6-diamino-(N,N,N',N'-tetraacetate)-3-nitroanisole An alkylated aminoanisole compound containing a nitro group in the aromatic ring (compound 4) was synthesized. The presence of the nitro group facilitates the molecular absorption in the visible region. Excitation wavelengths of 400 nm or above leading to fluorescence emission of about 450-500 nm prevents cell damage, reduces cost of equipment, and permits the visualization of the Zn-bound complex.

2,6-Dinitroanisole. 0.200 g (1.00 mmol) of commercially available 2-chloro-1,3-dinitrobenzene was dissolved in a warm solution of 15 ml methanol and 0.223 g (4.13 mmol) of NaOMe. The reaction was stirred overnight with continued warming. The residue was dissolved in water after evaporation of the solvent. The aqueous solution was extracted with dichloromethane, dried and evaporated under reduced pressure to give 0.187 g of 2,6-dinitroanisole (95%) as yellow flakes. $^1$H NMR (CDCl$_3$) δ 8.06 (d, J=8.2 Hz, 2H, Ar—H), 7.38 (t, J=8.2 Hz, 1H, Ar—H), 4.09 (s, 3H, O—CH$_3$). $^{13}$C NMR (CDCl$_3$) δ 148.0, 129.4, 124.2, 65.1.

2,6-Diaminoanisole. 0.500 g (2.52 mmol) of compound 2,6-dinitroanisole was suspended in 40 mL of water together with 2.310 g (35.3 mmol) of Zn and 0.530 g (10.1 mmol) of NH$_4$Cl. The solution was boiled for 2.5 h. After cooling to room temperature, the solution was extracted with ethyl acetate. The organic solution was dried with anhydrous Na$_2$SO$_4$ and distilled in vacuo to obtain 0.330 g (95%) of clean 2,6-diaminoanisole as a red oil. $^1$H NMR (CDCl$_3$) δ 6.73 (t, J=7.9 Hz, 1H, Ar—H), 6.19 (d, J=7.9 Hz, 2H, Ar—H), 3.78 (s, 3H, O—CH$_3$), 3.73 (br. s, 4H, Ar—NH$_2$). $^{13}$C NMR (CDCl$_3$) δ 140.3, 134.9, 125.2, 106.6, 58.6.

Ethyl-2,6-diamino-(N,N,N',N'-tetraacetate)anisole. 0.116 g (0.840 mmol) of 2,6-diaminoanisole was added to 14 mL of dried MeCN together with 0.830 g (5.04 mmol) of KI, 0.881 g (5.06 mmol) of K$_2$HPO$_4$, and 571 µL (5.00 mmol) of ethyl bromoacetate. Some molecular sieves were added and the solution was refluxed under air-free conditions (drying tube) for 33 h. The resulting mixture was filtered through a Buchner funnel loaded with SiO$_2$ using hexane-ethyl acetate (7:3). The filtrate was distilled and chromatographed over SiO$_2$ using hexane-ethyl acetate (95:5) mixture. 0.330 g (81%) of ethyl-2,6-diamino-(N,N,N',N'-tetraacetate)anisole was obtained as white crystals. $^1$H NMR (CDCl$_3$) δ 6.84 (t, J=8.2 Hz, 1H, Ar—H), 6.46 (d, J=8.2 Hz, 2H, Ar—H), 4.19 (q, J=7.2 Hz, 8H, C—CH$_2$—C), 4.16 (s, 8H, N—CH$_2$—C), 3.70 (s, 3H, O—CH$_3$), 1.27 (t, J=7.2 Hz, 12H, C—CH$_3$). $^{13}$C NMR (CDCl$_3$) δ 171.6, 144.2, 129.4, 124.2, 124.1, 112.7, 60.8, 54.0, 14.4.

Ethyl-2,6-diamino-(N,N,N',N'-tetraacetate)-3-nitroanisole. 0.080 g (0.166 mmol) of ethyl-2,6-diamino-(N,N,N',N'-tetraacetate)anisole was dissolved in 2 mL of Ac$_2$O. The solution was cooled to 0° C. in an ice-salt bath, followed by the addition of 13 µL (0.246 mmol) of HNO$_3$. The solution was stirred at room temperature for 1.5 h. The resulting mixture was cooled in ice, neutralized to pH 7 and warmed up to room temperature. The aqueous solution was extracted with dichloromethane and chromatographed over silica gel using hexane-ethyl acetate (9:1) to obtain 0.073 g (83%) of ethyl-2,6-diamino-(N,N,N', N'-tetraacetate)-4-nitroanisole as yellow-brown paste. $^1$H NMR (CDCl$_3$) δ 7.57 (d, J=9.3 Hz, 1H, Ar—H), 6.53 (d, J=9.3 Hz, 1H, Ar—H), 4.22-4.4.18 (m, 8H, C—CH$_2$—C; N—CH$_2$—C), 4.17-4.12 (m, 4H, C—CH$_2$—C), 4.00 (s, 4H, N—CH$_2$—C), 3.78 (s, 3H, O—CH$_3$), 1.30-1.22 (m, 12H, C—CH$_3$). $^{13}$C NMR (CDCl$_3$) δ 170.4, 170.3, 148.8, 146.6, 140.3, 139.0, 122.7, 112.6, 61.3, 61.0, 60.6, 55.1, 53.7, 14.4, 14.3.

Sodium 2,6-diamino-(N,N,N',N'-tetraacetate)-3-nitroanisole. 0.073 g (0.140 mmols) of ethyl-2,6-diamino-(N,N,N',N'-tetraacetate)-3-nitroanisole was dissolved in 6 mL methanol. Sodium carbonate (0.118 g, 1.11 mmol dissolved in 5 mL water) was added to the solution and the reaction mixture was stirred for 1 h. The solvents were removed under reduced pressure. The residue was dissolved in methanol and the insoluble excess sodium carbonate was removed by filtration. The methanol was removed under reduced pressure. Any remaining methanol was azeotroped with water. Yield 0.064 g (91%) of Sodium 2,6-diamino-(N,N, N',N'-tetraacetate)-3-nitroanisole as brown powder. $^1$H NMR (D$_2$O) δ 7.67 (d, J=9.6 Hz, 1H, Ar—H), 6.32 (d, J=9.6 Hz, 1H, Ar—H), 3.95 (s, 4H, —CH$_2$—), 3.84 (s, 4H, —CH$_2$—), 3.58 (s, 3H, O—CH$_3$). $^{13}$C NMR (D$_2$O) δ 178.3, 178.2, 151.1, 145.6, 125.9, 123.0, 112.3, 104.5, 63.5, 63.3, 54.6.

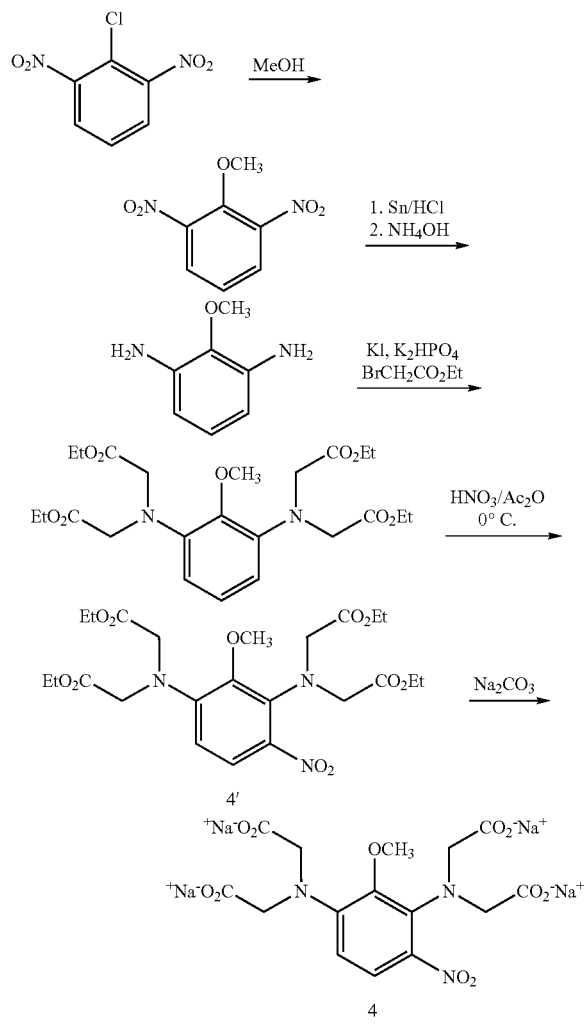

EXAMPLE 8

Fluorescence Profile of Sodium 2,6-diamino-(N,N,N',N'-tetraacetate)-3-nitroanisole (Compound 4)

Figure 4:
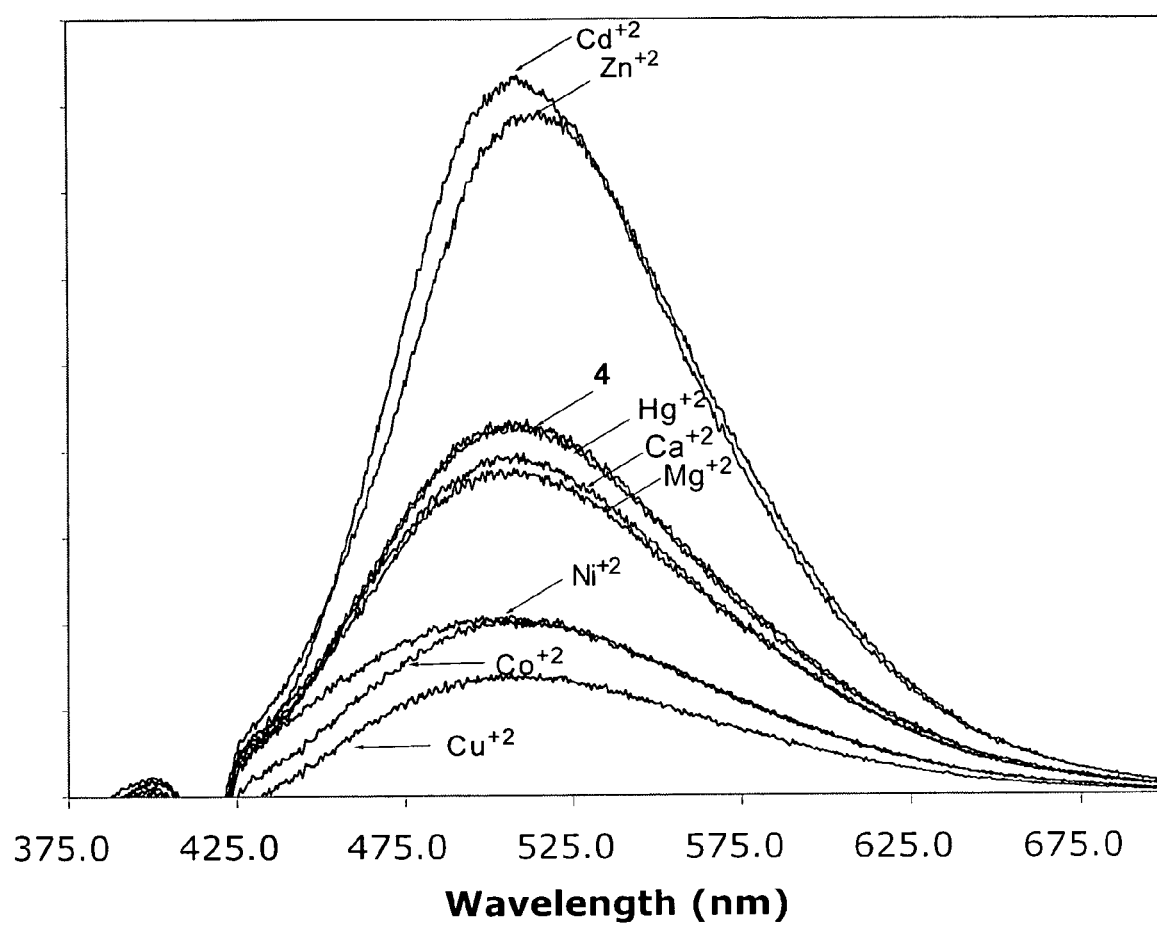
FIG. 4: Fluorescence emission spectra of compound 4.

The influence of divalent metal ions on the fluorescence spectral profile of compound is shown in FIG. 4, where the fluorescence emission spectra of 200 μM compound 1 ($\lambda_{ex}$=365 nm) with stoichiometric concentrations of selected divalent metal ions. Compound 4 has a UV absorption maximum at 425 nm. However, excitation at this wavelength does not lead to a fluorescence emission. Excitation at shorter wavelengths e.g. at 365 nm leads to a weak emission peak around 520 nm, which is differently affected by different metal ions. The emission intensity of compound 4 (at 520 nm) has no discernable effect in the presence of Hg$^{2+}$, it was slightly quenched by Mg$^{2+}$, Ca$^{2+}$. In contrast, as expected, the fluorescence intensity of compound 4 was significantly quenched in the presence of Cu$^{2+}$, Ni$^{2+}$, and Co$^{2+}$. In the presence of Zn$^{2+}$ and Cd$^{2+}$, the fluorescence of the compound is substantially enhanced.

The description of the specific embodiments of the invention is presented for the purpose of illustration. It is not intended to be exhaustive nor to limit the scope of the invention to the specific forms described herein. Although the invention has been described with reference to several embodiments, it will be understood by one of ordinary skill in the art that various modifications can be made without departing from the spirit and the scope of the invention, as set forth in the claims. All patents, patent applications and publications referenced herein are hereby incorporated by reference. Other embodiments are within the claims.

The invention claimed is:

1. A method for the detection of a metal ion selected from the group consisting of zinc ion and cadmium ion in a sample using a diamino polyacetate benzene compound as a metal ion sensor, comprising the steps of:
   a. incubating a sample containing the metal ion for a sufficient time to bind the metal ion with a diamino polyacetate benzene compound to form a complex;
   b. exciting the complex with light having a wavelength capable of causing emission of a fluorescent signal by the complex; and
   c. detecting the fluorescent signal emitted by the complex.

2. The method of claim 1, wherein the diamino polyacetate benzene compound includes an attached alkoxy group.

3. The method of claim 2, wherein the alkoxy group is a methoxy group.

4. The method of claim 3, wherein the diamino polyacetate benzene compound is compound 1.

5. The method of claim 2, wherein the diamino polyacetate benzene compound includes an attached nitro group.

6. The method of claim 5, wherein the nitro group is in a meta position with respect to the alkoxy group.

7. The method of claim 6, wherein the diamino polyacetate benzene compound is compound 4.

8. The method of claim 1, wherein the diamino polyacetate benzene compound is a diamino tetraacetate benzene compound.

9. The method of claim 8, wherein the diamino tetraacetate benzene compound is compound 3 of example 5.

10. The method of claim 1, wherein the diamino polyacetate benzene compound is a diamino triacetate benzene compound.

11. The method of claim 1, wherein the light is selected from a group consisting of visible light and ultraviolet light.

* * * * *